(12) United States Patent
Sirota et al.

(10) Patent No.: US 9,349,148 B2
(45) Date of Patent: May 24, 2016

(54) METHODS AND APPARATUS FOR ADAPTIVE MULTISENSOR ANALISIS AND AGGREGATION

(71) Applicants: Jacobo Marcos Sirota, Takoma Park, MD (US); Thomas Joseph Bouchard, Vienna, VA (US); Miodrag Cekic, Bethesda, MD (US); Cristopher Treadwell Field, Baltimore, MD (US)

(72) Inventors: Jacobo Marcos Sirota, Takoma Park, MD (US); Thomas Joseph Bouchard, Vienna, VA (US); Miodrag Cekic, Bethesda, MD (US); Cristopher Treadwell Field, Baltimore, MD (US)

(73) Assignee: Sigma Space Corp., Lanham, MD (US)

( * ) Notice: Subject to any disclaimer, the term of this patent is extended or adjusted under 35 U.S.C. 154(b) by 433 days.

(21) Appl. No.: 13/944,082

(22) Filed: Jul. 17, 2013

(65) Prior Publication Data

US 2015/0026023 A1  Jan. 22, 2015

(51) Int. Cl.
| | |
|---|---|
| *G01N 21/33* | (2006.01) |
| *G06Q 50/02* | (2012.01) |
| *G06Q 40/00* | (2012.01) |
| *G01S 17/89* | (2006.01) |
| *G01S 13/89* | (2006.01) |
| *G01N 33/24* | (2006.01) |
| *G01N 21/35* | (2014.01) |
| *G01N 21/17* | (2006.01) |
| *G01S 13/86* | (2006.01) |

(52) U.S. Cl.
CPC ............. *G06Q 50/02* (2013.01); *G06Q 40/00* (2013.01); *G01N 21/33* (2013.01); *G01N 21/35* (2013.01); *G01N 2021/1797* (2013.01); *G01N 2033/245* (2013.01); *G01S 13/86* (2013.01); *G01S 13/89* (2013.01); *G01S 17/89* (2013.01)

(58) Field of Classification Search
CPC ............. G01N 2021/1797; G01N 2033/245; G01N 21/33; G01N 21/35; G01P 3/36; G01S 13/86; G01S 13/89; G01S 17/89; G06Q 40/00; G06Q 50/02
USPC .......................................................... 705/35
See application file for complete search history.

(56) References Cited

U.S. PATENT DOCUMENTS

2014/0163772 A1* 6/2014 Vian .................... G05D 1/0094
701/2

* cited by examiner

*Primary Examiner* — Timothy A Brainard
(74) *Attorney, Agent, or Firm* — Intellectual Property Strategists, LLC; Miodrag Cekic (57) ABSTRACT

The present invention is directed to a self consistent method for adaptive implementation of overflying multi sensor measurements and derivation of conclusions and determinations "agregants", derived and/or developed from the measured results and/or resulting from science-based processing design to integrate and process the measured results and other data and scientific knowledge. Furthermore, the aggregants may be pertinent to determination of status and proactive management models of the at least one distributed resource by a single or repeatable implementation of one or several steps.

15 Claims, 8 Drawing Sheets

METHODS AND APPARATUS FOR ADAPTIVE MULTISENSOR ANALISIS AND AGGREGATION

CROSS REFERENCE TO RELATED APPLICATIONS

This application is based upon and claims benefits of U.S. Provisional Patent Application Ser. No. 61/683,304, entitled "METHODS AND APPARATUS FOR ADAPTIVE MULTISENSOR ANALISIS AND AGGREGATION" and filed with the U.S. Patent and Trademark Office on Feb. 15, 2011, and copendng and co-owned U.S. patent application Ser. No. 13/027,458 entitled "SELF-ORGANIZING SEQUENTIAL MEMORY PATTERN MACHINE AND REINFORCEMENT LEARNING METHOD" filed with the U.S. Patent and Trademark Office on Feb. 15, 2011, which are incorporated herein by reference.

FIELD OF THE INVENTION

The invention relates generally to methods and instruments for flexible adaptive multisensor data acquisitions and analysis of acquired information in order to generate results applicable to management of resources. In particular, the current invention pertains to a self consistent method for adaptive implementation of overflying multi sensor measurements and derivation of actionable conclusions pertinent to determination of status and proactive management models of at least one distributed resource associated to a geographic area.

BACKGROUND OF THE INVENTION

The instant invention pertains to methods which tie flexible data generation and retrieval, integrated data processing, analysis of extensive geographically-distinguishable databases and datasets, and advanced economic modeling and reporting, with nearly-real time financial management and/or financial services arranged to enable intelligent conduct of economic and social policies at scales ranging from single economic or political entities to global institutions and organizations.

The current invention enables development of flexible updatable knowledge management strategies and resulting actions that may be expended in space, time, or social importance to co-evolve with economic and social needs and dynamically respond to gradual or abrupt events and developments. In addition, benefits resulting from the current innovations may be utilized internally to address needs of groups and organizations actively involved and directly performing the methods and steps of the current invention or be marketed and delivered as a knowledge-based service to external clients or customers.

SUMMARY OF THE INVENTION

The present invention is directed to a self consistent method for adaptive implementation of overflying multi sensor measurements and derivation of conclusions and determinations, indicated herein as "agregants", derived and/or developed from the measured results and/or resulting from science-based processing design to integrate and process the measured results and other data and scientific knowledge. Furthermore, the aggregants may be pertinent to determination of status and proactive management models of the at least one distributed resource by a single or repeatable implementation of one or several steps such are listed below.

A step of providing at least one set of calibrated overflying multisensor detectors arranged for detecting signals from electromagnetic radiation redirected by a plurality of underlying structures having a combination of features having variable scale length.

A step of a) determining the at least one distributed resource of interest, an extent of the plurality of underlying structures, and a subcombination of features having a scale lengths of interest for derivation of the actionable aggregants pertinent to determination of status and proactive management of the at least one distributed resource of interest.

A step of b) determining and arranging a set of overflight parameters and arranging and preprogramming the at least one set of overflying multisensor detectors for detecting and processing signals from electromagnetic radiation redirected by the plurality of underlying structures having a combination of features having the scale lengths of interest.

A step of c) conducting the determined overflights and performing in-flight acquisition, preprocessing, and storing of data sets resulting from the multisensor measurements using the at least one set of overflying multisensor detectors.

A step of d) transferring the preprocessed data sets to at least one data analysis computing device and analyzing the transferred data sets using the determined set of overflight parameters and a set of predetermined overflying multisensor detectors calibration data.

A step of e) determining sufficiency of analyzed data sets for derivation of actionable aggregants pertinent to determination of status and proactive management of at least one distributed resource of interest; and, in a case of insufficient analyzed data sets, determining needs for additional data sets and repeating iteratively steps c)-e) until the sufficiency has been established.

A step of f) harmonizing the sufficient analyzed data sets corresponding to the underlying structures, the features, the scale lengths and the actionable aggregants of interest; and determining satisfactory consistency of the harmonized data sets; and, in a case of unsatisfactory consistency of harmonized data sets, determining needs for additional data sets and repeating iteratively steps c)-g) until the satisfactory consistency has been established.

A step of g) adding the consistent analyzed data sets into a database organized for storage and relational retrieval of data at least regarding the actionable aggregants, underlying structures, the features having the scale lengths of interest, and time.

A step of h) obtaining external data pertinent to the at least the actionable aggregants, underlying structures, the features having the scale lengths of interest, and time and adding it relationally into the database.

A step of i) constructing at least one economic model utilizing the at least one actionable aggregant pertinent to determination of status and proactive management models of at least one distributed resource;

A step of j) determining needs for updating the at least one economic model, and, in a case of positive determination of the updating need, repeating iteratively steps c)-j) until the up to date sufficiency has of the economic model has been established.

The present invention is also directed to devices and assemblies arranged to perform a set of aforementioned steps (or any individual step as required) and to risk assessment and management processes design to utilize the different implementations of the above method for various economic activities, leadership activities, and other activities design to benefit economic entities or public and social participants.

DETAILED DESCRIPTION

In the following description of embodiments of the present invention, numerous specific exemplary details are set forth in order to provide a more thorough understanding of the present invention. However, it will be apparent to one skilled in the art that the present invention may be practiced without one or more of these exemplary details. In other instances, well-known features of prior art have not been described in detail to avoid unnecessarily complicating the description.

Figure 1:
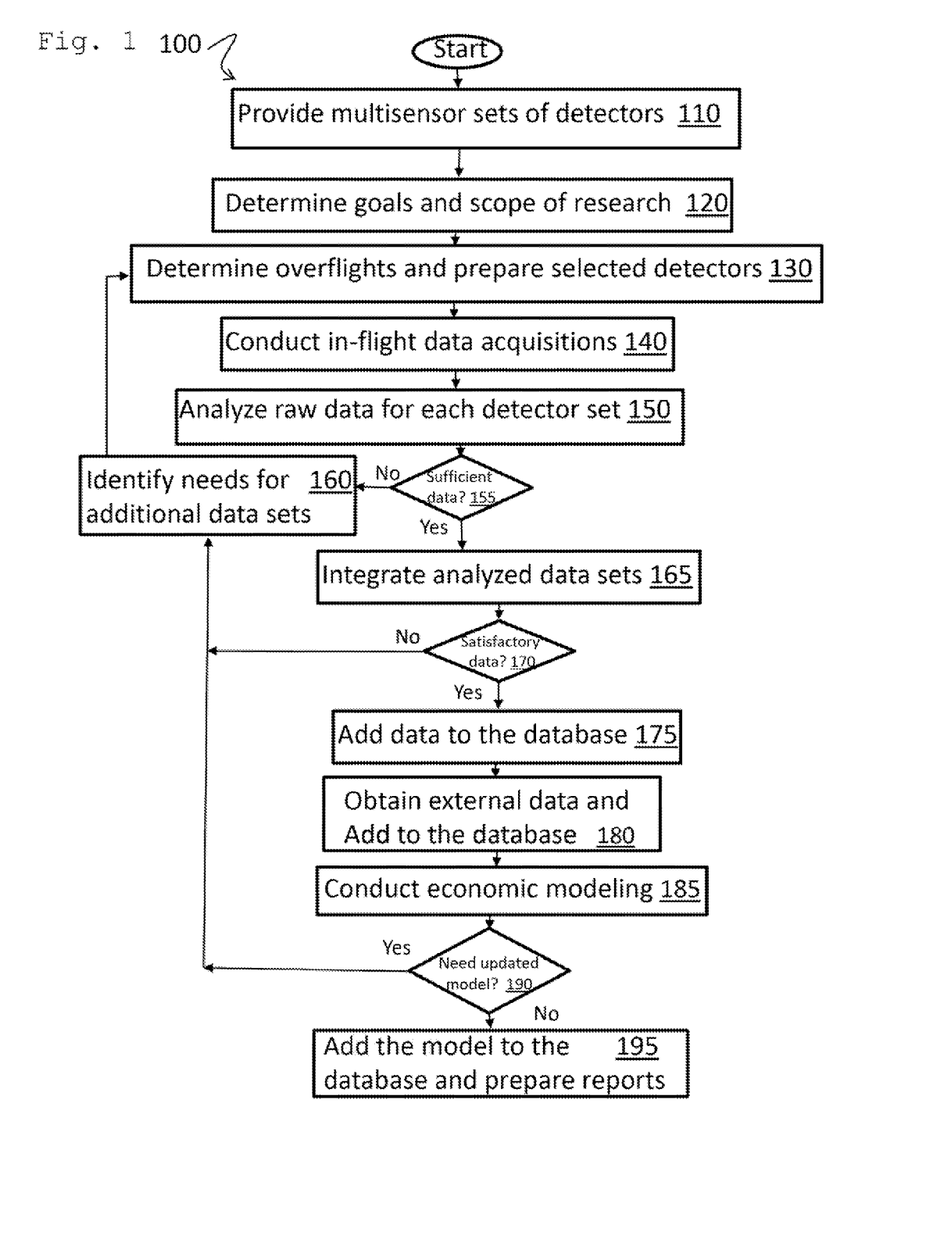
FIG. 1 is a schematic illustration of an exemplary embodiment of the present invention.

One particular self consistent method for adaptive implementation of overflying multi sensor measurements and derivation of conclusions and determinations aggregants pertinent to a group of embodiments of the present invention is illustrated schematically in the FIG. 1 flowchart 100. It includes the step 110 of providing at least one set of calibrated overflying multisensor detectors arranged for detecting signals from electromagnetic radiation redirected by a plurality of underlying structures having a combination of features having variable scale lengths. The set of multisensor detectors may be embodiment-specific and may include sensors and detectors arranged for installation on satellites, airplanes, helicopters, gliders, rockets, unmanned aerial vehicles, ballistic projectiles, aerostats (including kites, free and moored balloons, rigid and flexible airships), and variety of possible combinations (such are, but not limited to, kite/balloons known as "Helikites", motorized or rocket powered gliders known as "rocket-plans", free-dropping payloads, free-dropping or towed parachutes, par-gliders, motorized kites, light and micro-light kites/planes and similar).

Also, the multisensor detectors may be, according to the particular embodiment, purposely arranged and specialized for tusks of interest or multifunctional devices frequently provided by public or private institutions and available as public service or for use on commercial basis. It may be understood that the choice 110 of the set of detectors may be conceptual or flexible and may incorporate several options that may be implemented sequentially, in combination, and/or as alternatives, potentially changing in time and evolving in accordance with changes of goals or needs.

Furthermore, it may be noted that the set of overflying multisensor detectors may be arranged to function in support of, or being supported by additional stationary or surface-transportable detectors arranged to provide additional complementary, supporting, calibration, and/or verification measurements and resulting datasets. Even further, the relevant data may be obtained from historical record, databases, scientific and statistical models and modeled results, numerical simulations and similar.

It may be noted that a step of the choice of sets of overflying multisensor detectors may depend on particular embodiments. For one group of embodiments of the current invention the set of overflying multisensor detectors may be chosen from a group of detectors including visible, IR and UV spectrometers and spectro-photometers; visible, IR, and microwave radiometers, bolometers and spectrum analyzers, RADARs and Doppler RADARs; 2D and 3D LIDARs; and combinations of listed detectors.

In different groups of embodiments of the current invention pertinent to investigations of agricultural and food production resources the aggregants may be chosen from the set of aggregants incorporating soil type, soil curvature, soil-color class, soil texture, soil moisture, soil moisture index, seeding rate and seeding density, germination rate and density, difference vegetation index, normalize difference vegetation index, chlorophyll absorbance and reflectance, chlorophyll concentration and chlorosis factors, photosynthetic rate, observed and expected yields and yield density, covered or exposed surfaces albedo and spectral reflectance, plant or animal numbers and number density, and mixtures and combinations of the listed actionable aggregants.

Therefore, it may be noted that the particular determination of overflight parameters and choices of the sets of overflying multisensor detectors 130 may relate to goals and particular scopes of searches predetermined by potential parties of interest as motivated by particular needs and motivations to conduct particular investigations, modeling and management activities. Accordingly, at least initial determination of scopes and goals 120 of the inquiry to be conducted in the data acquisition stages of the methods in accordance with the current invention may be significant factor determining the overall success rate of the pertinent activities.

The overflight parameters pertinent to the application using space-bourn detector sets may include, but are not limited to, types of geocentric satellite orbit, altitude of geocentric orbit, eccentricity of elliptic geocentric orbit, synchronicity of geocentric orbit, inclination of geocentric orbit. In embodiments utilizing atmospheric areal flights the overflight parameters may include, for example, boundaries of atmospheric areal flight, time limits of atmospheric areal flight, operating altitude of atmospheric areal flight, ground velocity of atmospheric areal flight, and air velocity of atmospheric areal flight.

It may be noted that different embodiments may benefit from results derived from combinations of exo-atmospheric and areal detectors measurements. I may be likely that practitioners of methods according the o of current invention determining overflight parameters for such embodiments may use inherent relative flexibility of areal flight procedures to compensate for relative inflexibility of space-bourn instruments regarding spatial resolution, overflight timing, and/or scanning patterns. For example, the atmospheric areal overflights may be optimize to augment pertinent datasets available from satellite data basis, acquiring particular critical datasets revealing fine features regarded to be beyond the sensitivity limits of space-bourn detectors.

Regarding the step of conducting in-flight data acquisitions 140, one may deduce from above, that it may include segments of obtaining data acquired on extended or regular basis, for example using overflying satellites, and segments of purposely designed data acquisition targeting time and/or position specific information available, for example, only as a result of carefully designed and conducted searches. Consequently, a particular feature of the data acquisition in accordance with the methods of current invention may be related to flexibilities of the data acquisition scheme to react in nearly real time to the aggregate of preexisting information and in-streaming newly acquired results in order to augment and optimize resulting information versus predetermined or newly-evolved goals and scopes of the particular investigation.

Having in mind relative complexity and adaptability of devices and methods of various embodiments of current invention, it may be noted that different data analysis strategies and protocols for processing and analyzing 150 of raw data for all detectors may be utilized. In general, a preference for extensive in-situ data processing may be justified at least because of advantages related to optimization of speed, efficiency, reliability, and security of data transfers. Thus, in many embodiments, at least one data processing and data analysis computing device may be positioned in proximity of the sets of overflying multisensor detectors and arranged to process raw data sets transferred from overflying multisensor detectors, predetermined set of overflight parameters, and at least one set of predetermined overflying multisensor detectors calibration data.

In particular embodiments the acquired data may be communicated to remote processing computational devices for storage and further analysis. Also, one may expect that particular sets of embodiments may utilize appropriate combination of in-situ and remote data processing including a communication protocol enabling exchange of information such that improvements of data acquisition 140 and/or data analysis 150 may be effected in nearly real time.

It may be also noted that evaluation of sufficiency of processed and analyzed data, denoted by the decision block 155 in FIG. 1, may be performed in parallel or sequentially regarding the actions of the step 150. Again, recognizing potential complexities of the current method, it may be of interest to recognize potential insufficiencies in acquired datasets even during data acquisition step 140 such that corrective and/or remedial actions may be considered, planed and implemented even during contemporary overflights.

It may be also noted that more comprehensive versions of evaluation of processed data sufficiency may be performed subsequent to the active data acquisition 140 and raw data analysis 150 steps of various embodiments of the current method. One of significant results of the evaluation of the decision block 155 may be determination of quality of acquired information win emphasis on detected, probable, and/or apparent insufficiencies in the quality or structure of collected information such that needs for additional data sets may be identified (step 160). Timelines of such determination may be of particular interest considering the iterative features of the current method and potential advantages based on flexibility and adaptability of aforementioned and following steps and operations.

As a related note, a skilled practitioner may realize that the decision block 155 (as well as all subsequent decision blocks of the FIG. 1.) may not be strictly exclusive as customary in algorithms based exclusively on binary logic. Namely, it may be likely in some embodiments that particular segments of information as processed in the step 150 may be simultaneously or sequentially be directed both in the "No" direction to be used in step 160 and in the "Yes" direction to be timely analyzed and integrated in the step 165 (to the extent enabled by the inherent values and qualities of particular information segments).

Step 165 includes activities and processes of harmonizing the sufficient analyzed data sets resulting from the step 150. The integration may correspond to the underlying structures, the features, the scale lengths and the actionable aggregants of interest. Also, it may incorporate information regarding determined satisfactory consistency of the harmonized data sets, and, in a case of unsatisfactory consistency of harmonized data sets, needs for additional data sets as per step 160. It may be noted that an iterative repetition of aforementioned steps 130-160 may be performed until the sufficiency of the available data sets may be established, as schematically illustrated in FIG. 1 by the "Yes" direction of the decision block 155.

The step of evaluations corresponding to the decision block 170 may include further processing of the available data pertinent to evaluation of usefulness of the newly-generated data sets (for example, pertinent to the particular aggregants or groups of related aggregants) relative to the known features or previously determined information. Findings of significant discrepancies or contradictions, for example between different segments of newly-generated data sets or relative to the pre-existent data or previously-established findings and/or conclusions may result in an unsatisfactory determination ("No" of the decision block 170) which may require additional investigations yielding additional data sets as these aforementioned in discussions of the step 160. As evident from the flowchart 100, an expended iterative process including the steps 130-170 may be performed until the aforementioned difficulties may be overcame and satisfactory data obtained.

The step 175 pertains to actions of appropriate organization, storage, and preservation of the datasets emerging from the evaluations under the decision block 170 into at least one database structure. This step includes adding the consistent analyzed data sets into a database organized for storage and relational retrieval of data at least regarding the actionable aggregants, underlying structures, the features having the scale lengths of interest, and time. In addition, the step 175 may include actions directed toward planning, establishment, configuration, maintenance, upgrades, and management of software and hardware used for function and development of the at least one database, as well as several processes and activities directed toward communication and data exchange with other data-storage and processes activities of pertinent to other (e.g. external) publicly accessible or restricted-aces data processing establishments.

Subsequent step 180 concerns obtaining external data pertinent to the at least the actionable aggregants, underlying structures, the features having the scale lengths of interest, and time, and adding it relationally into the appropriate database or databases. This may include a broad variety of related data domains including, but not limited to, historic and time accumulated information, geological and/or climate records, economic and market statistics, demographic and public policy information, and/or integrated and multidisciplinary information and data combinations.

The step 185 pertains to processes and actions directed toward construction of at least one economic model utilizing the at least one actionable aggregant pertinent to determination of status and proactive management models of at least one distributed resource. It may be noted that scale, scope, complexity, goals, initial assumptions, and/or underplaying economic theories of the economic modeling 185 may strongly depend upon embodiment specific conditions, circumstances and limitations.

As an example, embodiments utilizing economic modeling based on "Hybrid-Maze" Simulation Model for Corn Growth and Yield commercially available from University of Nebraska, Lincoln, may require as input info: geolocation (position, size, elevation etc.) of the area of corn cultivation, particular time information (years, seasons, dates of interest for corn cultivation, historic wetter information, hydrological data pertinent to surface and underground wither deposits, meteorological records pertinent to atmospheric conditions (clouds, winds, aerosols, fugue, frosts . . . ), information related to pedology (including general soil typology, soil morphology, pedogenesis, edaphological features (including aspects pertinent to agrology, agrophysics, and "envirometology"—environmental soil science,) of the locality of interest. It may be of particular interest to provide accurate and up-to-date information on soil moister content (e.g. in the form of soil moister index obtainable, for example, from satellite or airborne radiometric measurements such are "SMOS" and "HYDROS" Satellites from NASA, or Passive and Active L- and S-band Radiometer (PALS) instruments flown on NSF's Lockheed (now Lockheed Martin) C-130 aircrafts).

The step of evaluation of needs for updating of available economic models, schematically indicated by the decision box 190 of FIG. 1, may include scheduled evaluations based on regularized schedules of data updates and/or reevaluation, and reevaluations induced by previously unforeseen or unplanned events including natural or men-caused emergences (e.g. floods, fires, storms, volcanic eruptions, economic and socio-political crises and disturbances, market instabilities, and similar conditions). It is a significant feature of the methods in accordance with the current invention that it may react flexibly and appropriately to virtually any change in conditions or demands all the way to those which may fundamentally alter the goals and scopes of the particular investigation. Furthermore, the above changes and flexibilities may be implemented such that substantially all valid preexisting data, information, processes, codes, databases, and concepts may be reused in existing or adapted forms for an efficient generation of new or updated concepts and pertinent supporting data. Therefore, embodiments of current invention may be responsible for up-to-date information enabling forecasting, risk analysis, planning, and/or near real time reaction in cases characterized by evolving, escalating, or crisis conditions.

In some applications of the current invention the updated economic models and pertinent information may be stored into relational databases and/or utilized for preparation of appropriate reports as in step 195 of the FIG. 1. It may be noted that the scope and contents of the report may strongly depend upon particular circumstances pertinent upon the inquiry of interest. It may be also noted that aforementioned features of timeliness and flexibility of the information generation process may be reflected in the reports of interest. As one example, the information generated by the methods of current invention may be used as an introductory, supplementary, or preliminary supplement for any monthly or periodic World Agricultural Supply and Demand Estimates (WASDE) Reports as available from U.S. Department of Agriculture Economics, Statistics and Market Information System (ES-MIS) as available, for example, from http://usda.mannlib.cornell.edu/MannUsda/viewDocumentInfo.do?documentID=1194, as at Jun. 24, 2012.

One group of embodiments of the methods in accordance with the current invention includes utilization of aforementioned 3D imaging LIDARs. Several generations of 3D imaging LIDARs have been developed and implemented by Sigma Space Corporation of Lanham, Md. Sigma personnel have more than a decade experience in developing a new class of scanning, single photon sensitive, 3D imaging LIDARs including:

$1^{st}$ Generation NASA/GSFC Microaltimeter (1999-2002)
$2^{nd}$ Generation USAF "Leafcutter" (2004-2007)
University of Texas "Icemapper" (2010)
NASA/GSFC Mini-ATM (2011-2012)
Sigma HRQLS (2012)
US Army Buckeye 2 (2012)

The characteristics of some of the above systems are summarized in following Table 1.

TABLE 1

| System Specifications | $2^{nd}$ Generation Scanning (USAF "Leafcutter" and U. of Texas "Icemapper") | NASA/GSFC Mini-ATM for Cryosphere Studies | Medium Altitude Scanning Sigma HRQLS | High Altitude Scanning US Army Buckeye 2 PC LIDAR |
|---|---|---|---|---|
| Host Platform | Aztec, King Air, DC 3 | Viking 300 UAV | King Air | Various |
| Nominal Above Ground Level (AGL) Range | 3 to 7 kft | 1.8 to 10 kft | 6.5-18 kft | 20-50 kft |
| Nominal Velocity | 87 knot | 56 knot | 200 knot | 200 knot |
| # beams/pixels | 100/100 | 100/25 | 100/100 | 100/100 |
| Laser Repetition Rate | To 22 kHz | 22 kHz | 25 kHz | 32 kHz |
| Measurements/sec | To 2,200,000 | To 550,000 | To 2,500,000 | To 3,200,000 |
| Full Scan Width Field Of View (FOV) | Variable 0 to 29° | Fixed 90° | Variable 0 to 40° | Fixed 18° |
| Swath vs AGL (at maximum FOV) | 0.47 to 1.1 km | 3 to 6.1 km | 1.4 to 4 km | 2 to 4.8 km |
| Areal Coverage vs AGL (at maximum FOV) | 76 to 177 km$^2$/hr | 200 to 632 km$^2$/hr | 600 to 1500 km$^2$/hr | 700 to 1750 km$^2$/hr |
| Mean Point Density vs AGL (at maximum FOV) | 90 to 6/m$^2$ (soil/veg) 300 to 30/m$^2$ (snow/ice) | 15 to 0.5/m$^2$ (snow/ice) | 18 to 2/m$^2$ (soil/veg) 18 to 6/m$^2$ (snow/ice) | 16 to 5/m$^2$ (soil/veg) 16 to 7/m$^2$ (snow/ice) |
| # of Modules | 2 | 1 | 1 (rack-mounted) | 1 (pod-mounted) |
| Dimensions/ Volume | Optical Bench, 13 × 12 × 17 in$^3$, 1.5 ft$^3$ | 0.94 ft$^3$ Quasi-cube | 19 × 25 × 33 in$^3$ (Rack Mount) | 18.2 ft$^3$ (19 × 25 × 66 in$^3$) |

TABLE 1-continued

| | | | | |
|---|---|---|---|---|
| | Electronics Box, 1 ft³ | | | |
| Weight | 73 lb | 28 lb | TBD | 250 lbs (est.) |
| Power Nominal | 266 W | 128 W | 555 W (est) | <900 W (est) |
| Peak (28 VDC) | 280 W | 148 W | | |
| Laser Output Power (full) | 140 mW 100 mW | | 1.7 W | 15 W |
| (per beam) | 1 mW | 1 mW | | |
| Wavelength | 532 nm | 532 nm | 532 nm | 532 nm |
| Pulse Width | 0.7 nsec | 0.7 nsec | 0.7 nsec | 0.1 nsec |
| Array Detector | 10 × 10 segmented anode MCP/PMT | 5 × 5 segmented anode MCP/PMT | 10 × 10 segmented anode MCP/PMT | 10 × 10 segmented anode MCP/PMT |
| Pixel Size | 1.6 mm × 1.6 mm | 1.6 mm × 1.6 mm | 1.6 mm × 1.6 mm | 1.6 mm × 1.6 mm |
| Pixel Resolution | USAF: 0.15 mrad × 0.15 mrad Texas: 0.3 mrad × 0.3 mrad | 0.3 mrad × 0.3 mrad | 0.2 mrad × 0.2 mrad | 0.06 mrad × 0.06 mrad |
| Fame rate | 22 kHz | 22 KhZ | 22 kHz | 22 kHz |
| Signal to Noise Resolution (SNR) | Single Photon Sensitivity | Single Photon Sensitivity | Single Photon Sensitivity | Single Photon Sensitivity |
| Timer Resolution | ±0.08 nsec | ±0.04 nsec | ±0.04 nsec | ±0.04 nsec |
| Time Synchronization | To GPS 1pps | To GPS 1pps | To GPS 1pps | To GPS 1pps |
| In-rush current | <15 A | 6 A | TBD | TBD |
| Command | RS232 through USB or Ethernet to RS232 converter | RS232 through USB or Ethernet to RS232 converter | RS232 through USB or Ethernet to RS232 converter | RS232 through USB or Ethernet to RS232 converter |
| Telemetry | Data storage on intenal solid state drive. Health through RS232. | Data storage on internal solid state drive. Health through RS232. | Data storage on internal solid state drive. Health through RS232. | Data storage on internal solid state drive. Health through RS232. |
| Command bandwidth | 119 kB Few dozen bytes required to start/stop data collection. | 119 kB. Few dozen bytes required to start/ stop data collection. | 119 kB. Few dozen bytes required to start/stop data collection. | 119 kB. Few dozen bytes required to start/stop data collection. |
| Maximum telemetry bandwidth | 119 kB for quicklook data (~0.2%) and health. | 119 kB for quicklook data (~0.2%) and health. | 119 kB for quicklook data (~0.2%) and health. | 119 kB for quicklook data (~0.2%) and health. |
| Maximum raw data rate | Data transfer to disk over two 40 MBPS IDE disk interface. Average rate ~6.5 MBPS). Optical interface (>1 GbPS) | Data transfer to disk over two 40 MBPS IDE disk interface. Average rate ~6.5 MBPS). Optical interface (>1 GbPS) | Data transfer to disk over two 40 MBPS IDE disk interface. Average rate ~6.5 MBPS). Optical interface (>1 GbPS) | Data transfer to disk over two 40 MBPS IDE disk interface. Average rate ~6.5 MBPS). Optical interface (>1 GbPS) |
| Data Latency | Data buffered into 32 MB blocks for transfer to disk. Latency can be as short as s 5 sec. or as long as 70 sec depending on event rate. | Data buffered into 32 MB blocks for transfer to disk. Latency can be as short as 5 sec. or as long as 70 sec depending on event rate. | Data buffered into 32 MB blocks for transfer to disk. Latency can be as short as 5 sec. or as long as 70 sec depending on event rarte. | Data buffered into 32 MB blocks for transfer to disk. Latency can be as short as 5 sec. or as long as 70 sec depending on event rate. |
| Temperature Range | 15 to 30 C. | 0 to 30 C | 0 to 30 C. | 0 to 30 C. |

All the systems tabulated above have been designed to provide high efficiency, high resolution 3D LIDAR imaging. Use of single photon sensitive microchannel plate photomultipliers, combined with our in-house low deadtime timing receivers, allows for operations in high solar noise environments and to penetrate obscurants such as thin clouds, ground fog, battlefield dust, and tree canopies. The 532 nm wavelength may take advantage of sensitive, low noise, fast recovery array detectors and efficient spectral filters available only in the visible wavelength regime. The segmented anode photomultipliers, combined with dual wedge optical scanners, allow for coverage of large FOVs with high spatial resolution and measurement rates measured in Megapixels per second. The highly flexible scanners can be used to generate contiguous 3D images on a single overflight from high velocity aircraft (with linear raster or conical scans) or from a quasi-stationary platform in 3D camera mode (using rotating line or spiral scans).

Figure 2A:
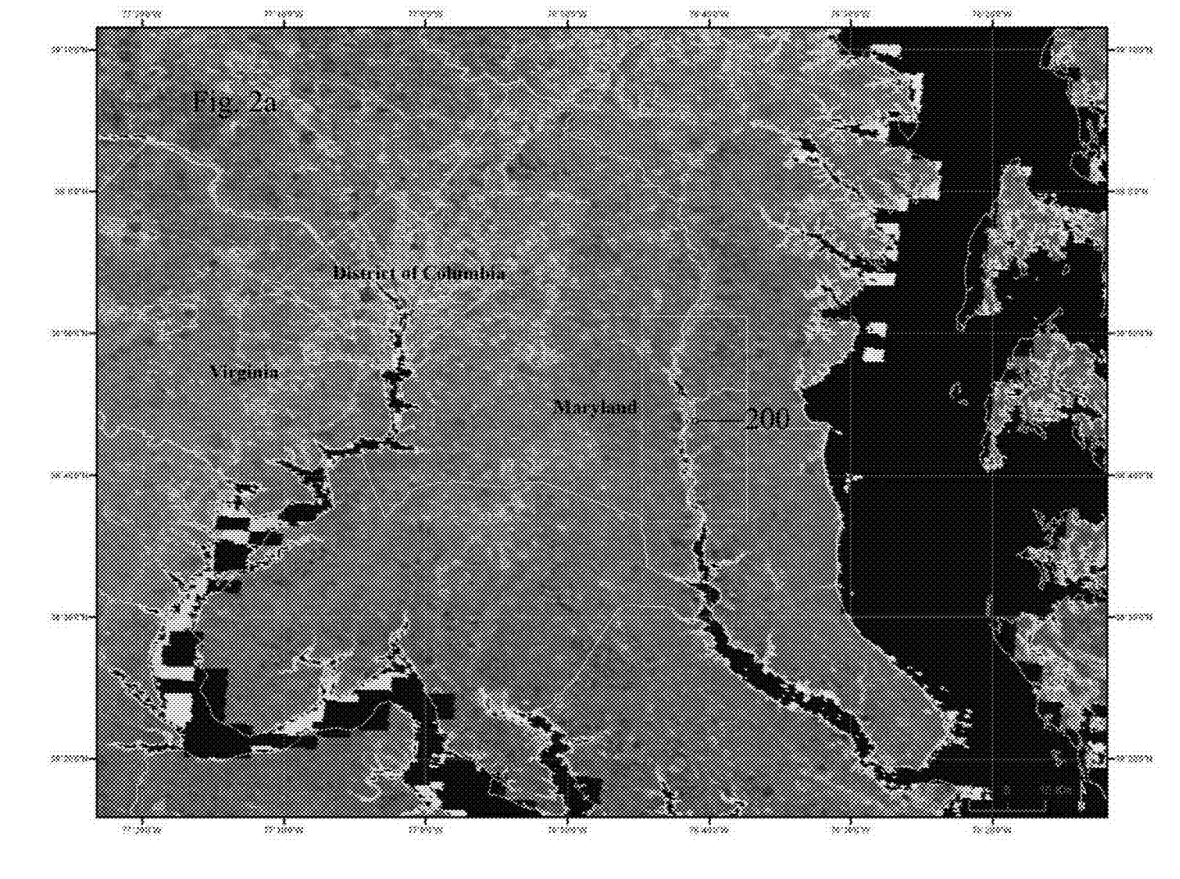
FIG. 2a-b are illustrations of a different exemplary embodiment of the present invention.
Figure 2B:
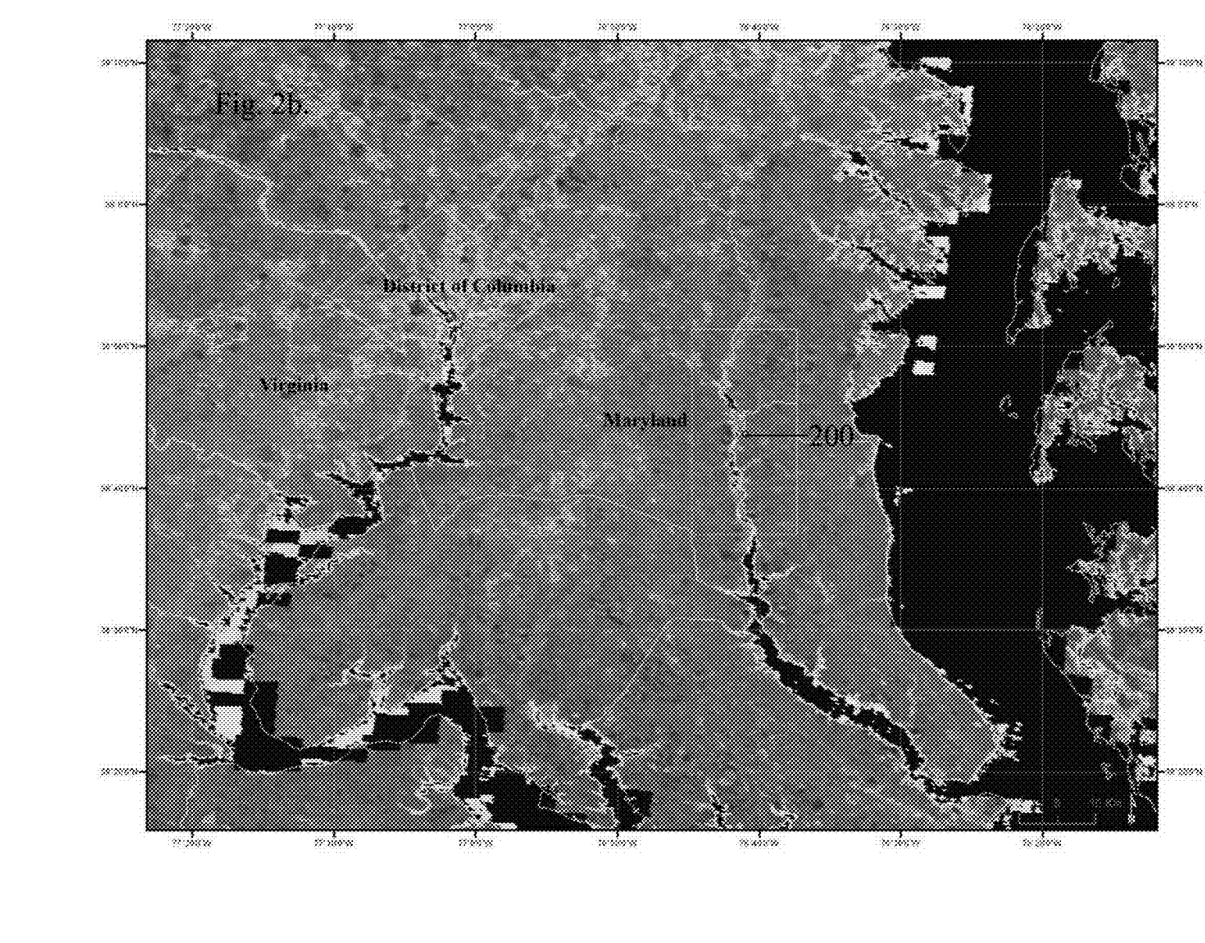

An example of an embodiment incorporating space-bourn data acquisition is illustrated in FIGS. 2a-b. The images in FIGS. 2a-b represent gridded Normalized Difference Vegetation Index (NDVI) data used customarily in remote sensing application as a representative (reciprocal) measure of photosynthetic activities associated with surface areas of interest. The illustrated NDVI in FIGS. 2a-b (given as a grading in false gray color such that darker hues represent decreasing values of NDVI=(NIR−VIS)/(NIR+VIS), normalized reflectance in Near Infra Read (NIR) and VISible (VIS) in appropriate segments of measured reflectance spectrum.

The data in FIGS. 2a-b have been generated as 16 day composites of measurements from the MODIS instrument of the Aqua satellite with 250 m resolution (MODIS VI, product from the MOD13Q1 database available for example from NASA) over the common 1200 km×1200 km area of Eastern U.S. The illustrated datasets indicate NDVI mostly during April (a), July (b), and October (c) of 2011, and include a point of interest 200 in Eastern Maryland proximal to the 38° 43' 50" N Latitude and 76° 41' 02" W Longitude.

It may be noted without a detailed analysis that FIGS. 2a-b indicate generally self-similar feature that arboreal, grazing/movable, and/or cultivated lands differ significantly in the NDVI related aggregants from urbanized or "developed" lands or water surfaces, but the selected scale lengths and resolutions may be relatively insensitive to ("normal") seasonal or vegetative cycles related changes especially over the areas exhibiting diversities characteristic of Eastern/Mid-Atlantic region of the United States. In particular, very limited information may be available on the particular locality of interest proximal to the 38° 43' 50" N Latitude and 76° 41' 02" W Longitude, predominantly because of the choice of the MODIS instrument and it's spatial and temporal resolutions.

Figure 3A:
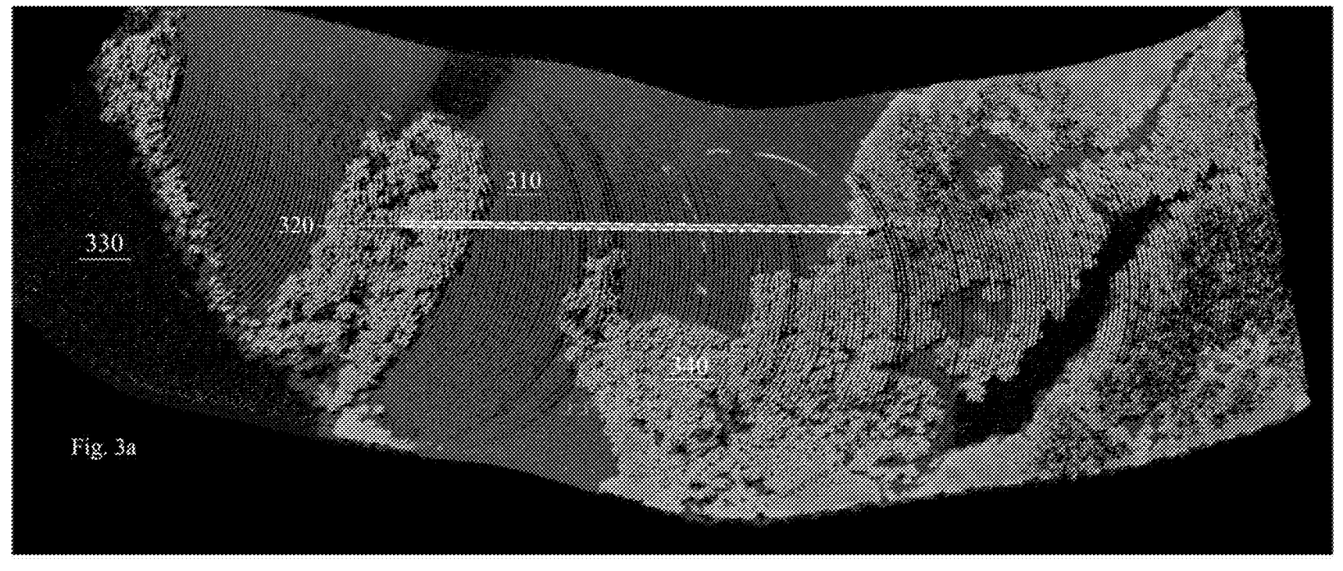
FIG. 3a-b are illustrations of another different exemplary embodiment of the present invention.
Figure 3B:
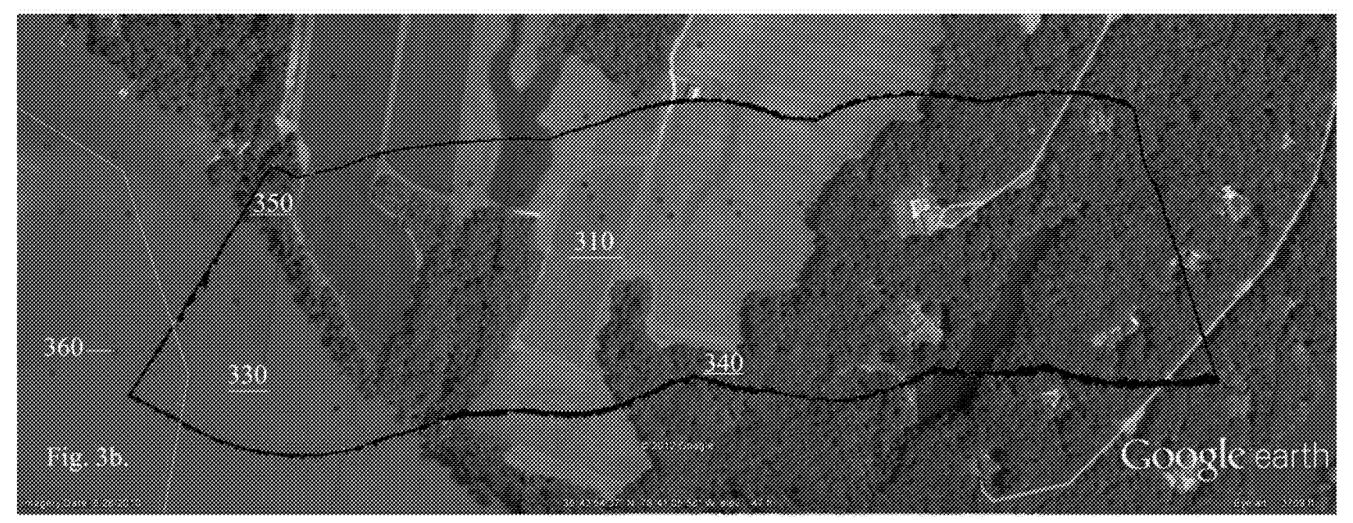

Other embodiments my relate to more detailed rendering of features associated to the proximity of the point of interest at 38° 43' 50" N Latitude and 76° 41' 02" W Longitude. One example utilizing data collected by the aforementioned University of Texas "Icemapper" operated in 3D LIDAR conical scan camera mode is illustrated in FIG. 3a-b. FIG. 3a illustrates a portion of aggregated data generated during a Beechcraft King Air 90C airplane 700 m overflight on Oct. 23, 2011. The illustrated features may be more convenient to interpret from the information in FIG. 3b having the scan area 350 of the FIG. 3a superimposed on an aerial photo as available (Jun. 28, 2012) from the "Google earth" web application of Google Inc. registered at 1600 Amphitheatre Parkway Mountain View, Calif. 94043. In addition, in FIG. 3b one may note position markers 360 indicative of the surface projections of the position of the Beechcraft King Air 90C airplane at the particular time of proximal 3D LIDAR data acquisition.

The 3D LIDAR scene in FIG. 3a includes a corn field 310 separated from the Patuxent River 330 by arboreal areas 340. It may be noted that FIG. 3a also include an indicator 320 marking the data portion used for generation of vertical profiles illustrated in FIG. 4a-c. Three vertical profiles a-c have been recorded during three distinct phases of corn vegetative cycle, of which FIG. 4a may be correlated to germination and seedling early development phase (spring of 2011), FIG. 4b may be correlated to full grown cob bearing phase of mature corn (Jul. 15, 2011), while FIG. 4c relates to the corn field 310 after the corn has been harvested (Oct. 23, 2011).

Figure 4A:
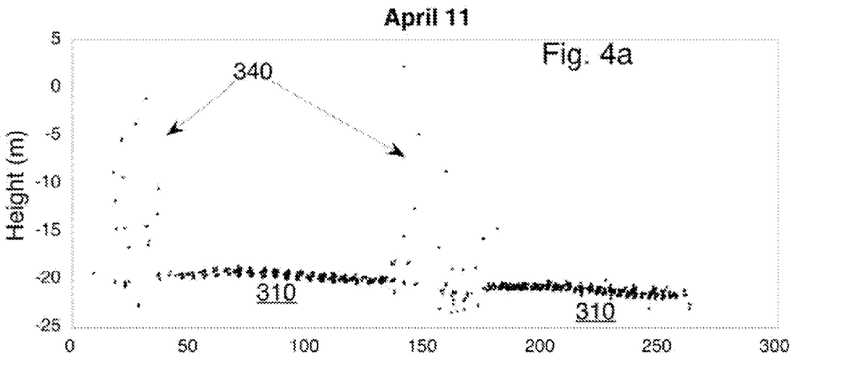
FIG. 4a-c are illustrations of yet another different exemplary embodiment of the present invention.
Figure 4B:
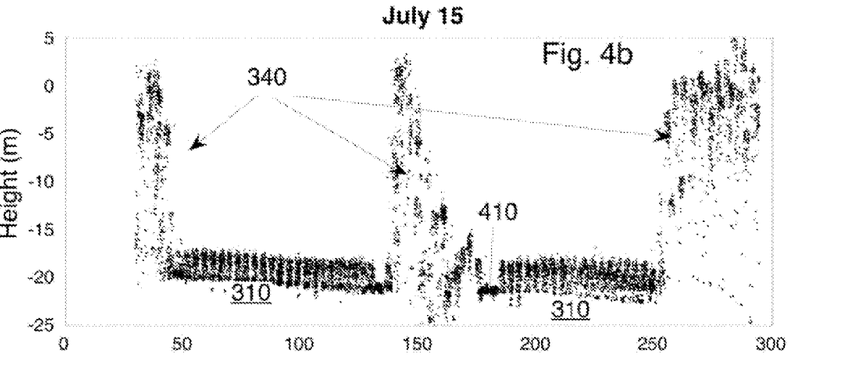
Figure 4C:
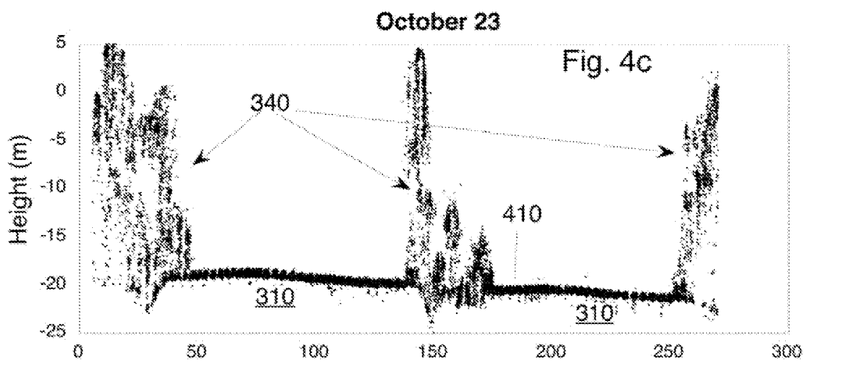

It may be of interest to note that FIG. 4a, pertinent to corn germination and seedling sprouting and early development phase (spring of 2011) may be used as a basis for determination of ground level and its gradients mostly conditioned by the presence of the Patuxent River 330. It may be noted that the profiles in FIG. 4a-c have been inverted with respect to the indicator 320 of FIG. 3a. Namely, the profiles in FIG. 4a-c are plotted such that the abscissa is pointing generally into westerly direction (toward the closest bank of the Patuxent River 330) such that ground level of the corn field 310 rises in the opposite direction. For that purpose, the data points associated with the arboreal areas 340 at larger x values ("the right side" of the profile in FIG. 4a) have been filtered out and not included in the FIG. 4a, but distinguishable in FIGS. 4b-c.

In addition, one can note significant corn field 310 related features including one of access roads surface 410 associated with the edges of the field 310. Also, a detailed statistical analysis of the data, particularly in FIG. 4b may be used for yield estimates (both corn cub and corn total biomass related) up to estimates of harvest losses and residues (for example in FIG. 4c).

Figure 5A:
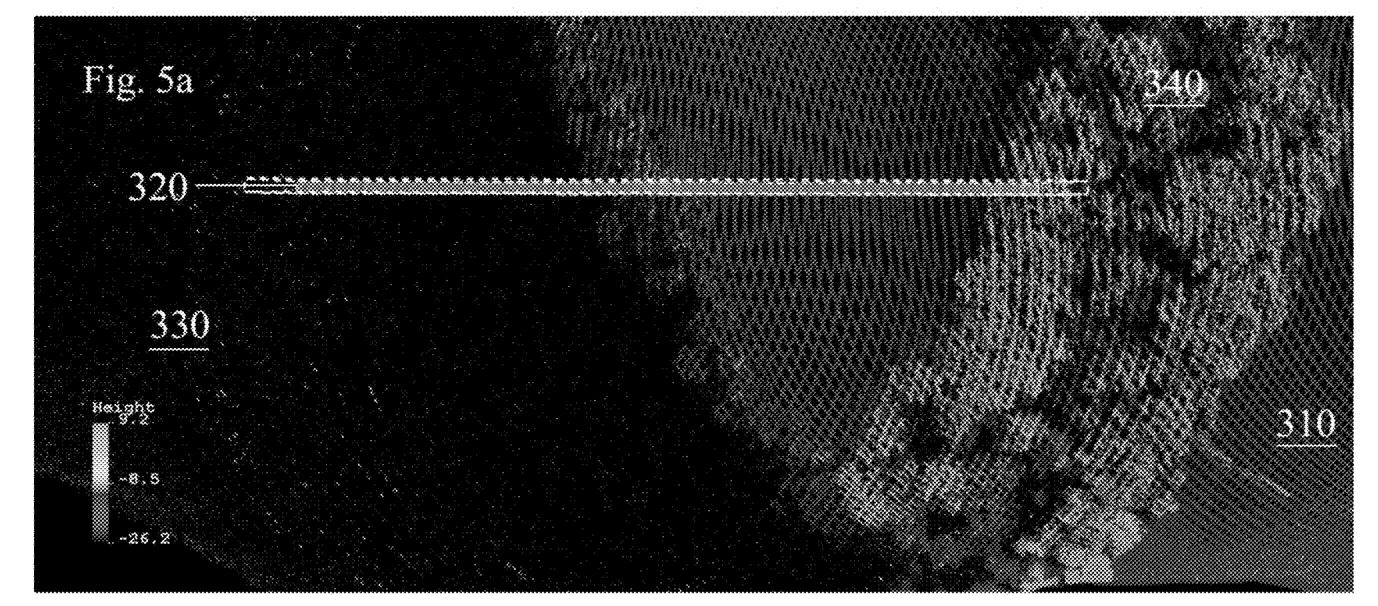
FIG. 5a-b are illustrations of yet another different exemplary embodiment of the present invention.
Figure 5B:
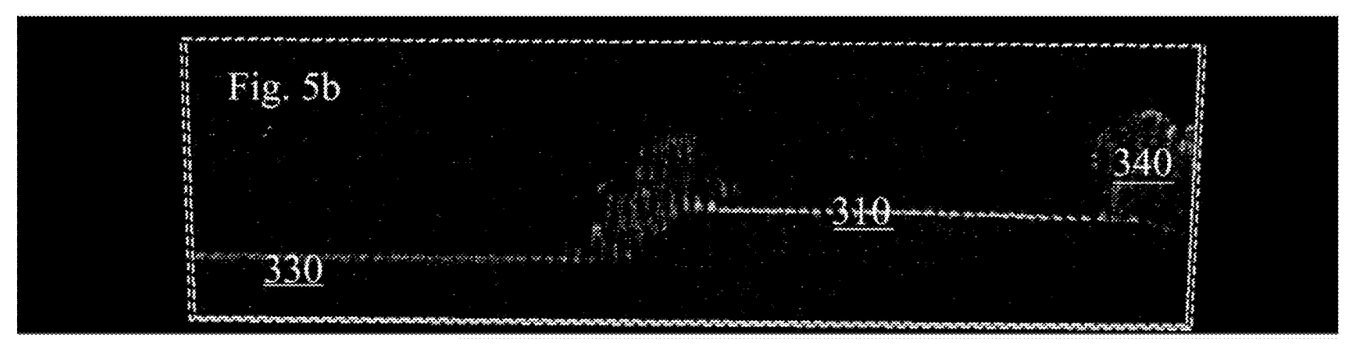

In different embodiments, detailed investigation of water surfaces may be conducted using 3D LIDAR imaging techniques. In an exemplary embodiment illustrated in FIGS. 5a (surface projection) and 5b (vertical cross-section) of waters and embankment of aforementioned Patuxent River 330 proximal to the position of interest 38° 43' 50" N Latitude and 76° 41' 02" W Longitude have been illustrated. One may note that a systematic survey of this particular kind may yield data pertinent to surface and underground water flow, pollution, erosion, soil moister index, and other aggregants.

Furthermore, in embodiments utilizing combination of different aforementioned detectors and detector combinations, an issue of combining results from different detector measurements may be of importance. In such embodiments, information generated by multiple detectors measuring common areas of interest may be imputed into a hierarchical network such is the network 20 of FIG. 1 of the incorporated copending U.S. patent application Ser. No. 13/027,458, for pattern analysis and subsequent processing. In similar embodiments, the different detectors outputs may be inputted in individual networks 20 forming a network of networks as illustrated in FIG. 6 of the above incorporated patent application.

The present invention has been described with references to the above exemplary embodiments. While specific values, relationships, materials and steps have been set forth for purpose of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

We claim:

1. A method for adaptive implementation of overflying multi sensor measurements and derivation of actionable aggregants pertinent to determination of status and proactive management models of at least one distributed resource comprising steps of:
   a) providing at least one set of calibrated overflying multisensor detectors arranged for detecting signals from electromagnetic radiation redirected by a plurality of underlying structures having a combination of features having variable scale lengths;
   b) determining the at least one distributed resource of interest, an extent of the plurality of underlying structures, and a subcombination of features having a scale lengths of interest for derivation of the actionable aggregants pertinent to determination of status and proactive management of the at least one distributed resource of interest;
   c) determining and arranging a set of overflight parameters and arranging and preprogramming the at least one set of overflying multisensor detectors for detecting and processing signals from electromagnetic radiation redirected by the plurality of underlying structures having a combination of features having the scale lengths of interest;
   d) conducting the determined overflights and performing in-flight acquisition, preprocessing, and storing of data sets resulting from the multisensor measurements using the at least one set of overflying multisensor detectors;
   e) transferring the preprocessed data sets to at least one data analysis computing device and analyzing the transferred data sets using the determined set of overflight parameters and a set of predetermined overflying multisensor detectors calibration data;
   f) determining sufficiency of analyzed data sets for derivation of actionable aggregants pertinent to determination of status and proactive management of at least one distributed resource of interest; and, in a case of insufficient analyzed data sets, determining needs for additional data sets and repeating iteratively steps c)-f) until the sufficiency of analyzed data set has been established;
   g) harmonizing the sufficient analyzed data sets corresponding to the underlying structures, the features, the scale lengths and the actionable aggregants of interest; and determining satisfactory consistency of the harmonized data sets; and, in a case of unsatisfactory consistency of harmonized data sets, determining needs for additional data sets and repeating iteratively steps c)-g) until the satisfactory consistency has been established;
   h) adding the consistent analyzed data sets into a database organized for storage and relational retrieval of data at least regarding the actionable aggregants, underlying structures, the features having the scale lengths of interest, and time;
   i) obtaining external data pertinent to at least the actionable aggregants, underlying structures, the features having the scale lengths of interest, and time and adding it relationally into the database;
   j) constructing at least one economic model utilizing the at least one actionable aggregant pertinent to determination of status and proactive management models of at least one distributed resource;
   k) determining needs for updating the at least one economic model, and, in a case of positive determination of the updating need, repeating iteratively steps c)-j) until an up to date sufficiency of the economic model has been established.

2. The method of claim 1, further comprising step of adding of the up to date economic models into the database and using the up to date economic models to compose a plurality of periodic or on-demand reports.

3. The method of claim 1, wherein the at least one distributed resource has been chosen from a set of distributed resources consisting of: amount of arable land dedicated to particular crop or left fallow; volume of stored water available for water supply, irrigation, and energy generation; amount of ice and snow cover; biomass supported by forested land or non-arboreal land supporting trees, vines, shrubs, and grasses; population of free-running or aqua-cultured fish and protein-bearing species; number and population density of wild animals, domesticated animals or invasive creatures: distributions and concentrations of pollutants, hazardous materials, and pest creatures; and combinations of the listed resources.

4. The method of claim 1, wherein the at least one set of calibrated overflying multisensor detectors has been chosen from a group of detectors consisting of: visible, IR and UV spectrometers and spectrophotometers; visible, IR, and microwave radiometers, bolometers and spectrum analyzers, RADARS and Doppler RADARs; 2D and 3D LIDARs; and combinations of listed detectors.

5. The method of claim 1, wherein the at least one detector from the set of calibrated overflying multisensor detectors includes a directional scanner arranged for selective detecting of signals from electromagnetic radiation redirected by a particular underlying structures having a particular feature having a predetermined scale length.

6. The method of claim 5, wherein the at least one detector from the set of calibrated overflying multisensor detectors includes a 3D imaging LIDAR.

7. The method of claim 6, wherein the 3D imaging LIDAR is arranged to perform up to 3,200,000 measurements per second.

8. The method of claim 6, wherein the 3D imaging LIDAR is arrranged to have a best pixel resolution of $0.06 \times 0.06$ mrad.

9. The method of claim 6, wherein the 3D imaging LIDAR is arranged to have a best time resolution of $\pm 0.04$ nsec.

10. The method of claim 6, wherein the 3D imaging LIDAR is arranged to have a Nominal Above Ground Level up to 50000 ft.

11. The method of claim 6, wherein the 3D imaging LIDAR is arranged to have an Areal Coverage versus Above Ground Level up to 1750 $km^2$/hr.

12. The method of claim 1, wherein the actionable aggregants are chosen from the set of aggregants consisting of soil type, soil curvature, soil-color class, soil texture, soil moisture, soil moisture index, seeding rate and seeding density, germination rate and density, difference vegetation index, normalize difference vegetation index, chlorophyll absorbance and reflectance, chlorophyll concentration and chlorosis factors, photosynthetic rate, observed and expected yields and yield density, covered or exposed surfaces albedo and spectral reflectance, plant or animal numbers and number density, and mixtures and combinations of the listed actionable aggregants.

13. The method of claim 12, wherein the observed and expected yields and yield density include yields of agricultural commodities selected from the group of commodities consisting of corn, oats, rice, soybeans, wheat, rapeseed, cotton, cocoa, coffee, sugar cane and sugar beet, and oranges.

14. The method of claim 13, wherein the observed and expected yields and yield density are arranged as input data to the economic models yielding results and parameters from the set of parameters consisting of: estimates of global and/or local inventories and supplies the agricultural commodities; global or local current production estimates of the agricultural commodities, availability/maturity dynamics of yields of the agricultural commodities in time, uncertainty and risk estimates and dynamics of uncertainty changes associated with supplies and production estimates of the agricultural commodities, and estimates of spot and future prices of the agricultural commodities.

15. The method of claim 1, wherein the set of overflight parameters has been selected from the group consisting of: type of geocentric satellite orbit, altitude of geocentric orbit, eccentricity of elliptic geocentric orbit, synchronicity of geocentric orbit, inclination of geocentric orbit, boundaries of atmospheric areal flight, time limits of atmospheric areal flight, operating altitude of atmospheric areal flight, ground velocity of atmospheric areal flight, and air velocity of atmospheric areal flight.

* * * * *